United States Patent [19]
Dietz

[11] Patent Number: 5,814,500
[45] Date of Patent: Sep. 29, 1998

[54] DELIVERY CONSTRUCT FOR ANTISENSE NUCLEIC ACIDS AND METHODS OF USE

[75] Inventor: Harry C. Dietz, Towson, Md.

[73] Assignee: The Johns Hopkins University School of Medicine, Baltimore, Md.

[21] Appl. No.: 742,943

[22] Filed: Oct. 31, 1996

[51] Int. Cl.$^6$ .................................................. C12Q 1/02
[52] U.S. Cl. ...................... 435/172.3; 435/6; 435/320.1; 536/24.1; 536/24.5
[58] Field of Search ................................. 536/23.1, 23.5, 536/24.5, 24.1; 435/6, 172.3; 514/44

[56] References Cited

U.S. PATENT DOCUMENTS

| | | | |
|---|---|---|---|
| 5,500,357 | 3/1996 | Taira et al. | 435/91.31 |
| 5,624,803 | 4/1997 | Noonberg et al. | 435/6 |

OTHER PUBLICATIONS

Michienzi, et al., U1 small nuclear RNA chimeric ribozymes with substrate specificity for the Rev pre–mRNA of human immunodeficiency virus, *Proc. Natl. Acad. Sci. USA*, 93:7219, Jul. 1996.

Bertrand, et al., Can Hammerhead ribozymes be efficient tools to inactive gene function?, *Nucleic Acids Research*, 22(3):293, 1994.

Perlick, et al., American Society of Human Genetic Meeting, San Francisco, Nov. 1, 1996.

Montgomery, et al., American Society of Human Genetic Meeting, San Francisco, Oct. 31, 1996.

De Young et al. Functional characterization of ribozymes expressed unsing U1 and T7 vectors for the intracellular cleavage of ANF mRNA. Biochem., vol. 33, pp. 12127–12138, 1994.

Barinaga, Marcia Ribozymes: Killing the Messenger. Science, vol. 262, pp. 1512–1514, Dec. 3, 1993.

Gura, Trisha Antisense has growing pains. Science, vol. 270, pp. 575–577, Oct. 27, 1995.

Baserga and Steitz, (1993), "The Diverse World of Small Ribonucleoproteins," *The RNA World*, Cold Spring Harbor Laboratory Press, New York, pp. 359–381.

*Primary Examiner*—Jasemine C. Chambers
*Assistant Examiner*—Deborah J. R. Clark
*Attorney, Agent, or Firm*—Fish & Richardson P.C.

[57] ABSTRACT

A novel nucleic acid construct for delivery of antisense targeting sequences is provided. The construct includes intact stem loop structures and an antisense nucleic acid. Optionally, a ribozyme nucleic acid is included in the construct. The construct is useful for inhibition of selected genes in a cell. This allele-specific targeting is also useful in combination with replacement gene therapy.

11 Claims, 4 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:1:

```
AATTGGCGAT  CTCCAGCACT  GATGAGTCCG  TGAGGACGAA  ACGCCCTCGA  CGCAT                55
```

( 2 ) INFORMATION FOR SEQ ID NO:2:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:2:

```
CTAGATGCGT  CGAGGGCGTT  TCGTCCTCAC  GGACTCATCA  GTGCTGGAGA  TCGCC                55
```

DELIVERY CONSTRUCT FOR ANTISENSE NUCLEIC ACIDS AND METHODS OF USE

FIELD OF THE INVENTION

This invention relates generally to the field of delivery vehicles for nucleic acid molecules and specifically to a novel construct for delivery of antisense targeting sequences to a cell.

BACKGROUND OF THE INVENTION

The use of antisense oligonucleotides offers advantages over other therapeutic regimes due to their potential for target specificity. For example, conventional chemotherapy for neoplastic and virus-related diseases has the disadvantage of systemic toxicity. The therapeutic index for chemotherapeutic agents is relatively narrow, since such agents are unable to distinguish between normal and diseased cells. Antisense oligonucleotides have the potential to be many orders of magnitude more specific than traditional drugs due to their greater number of interactions with a particular target site. In theory, an oligonucleotide of more than 15–17 nucleotides in length could have the base pairing specificity to interact with only one target gene within the entire human genome. Thus, antisense oligonucleotides have the potential specificity that could serve as a powerful tool for the study of specific gene function and as therapeutic agents for disease-causing genes.

In contrast to drugs, antisense molecules are relatively simple to design. The interaction between an antisense oligonucleotide and a target mRNA is governed primarily by the sequence of the target. Oligonucleotides targeting the start codon and extending upstream or downstream have been shown to be effective. Similarly, oligonucleotides that are complementary to the splice sites have proved effective.

Antisense technologies for the targeted inhibition of gene expression could provide an effective strategy for the management of inherited disorders with dominant-negative or gain-of-function pathogenetic mechanisms, for the suppression of oncogenes, or for the control of a variety of infectious agents. Pathologic disorders that are currently targeted by antisense therapeutics include viral infections, inflammatory disorders, cardiovascular disease, cancers, genetic disorders and autoimmune diseases. Synthetic oligodeoxynucleotides (ODNs), especially phosphorothiates and methylphosphonates, offer the advantage of enhanced stability in biological fluids and an effectively limitless supply.

Antisense oligonucleotides are also useful for the production of transgenic animals having alterations at the germline level, such as knockout mutations, which can be used for the study of new genes or the study of the function of a known gene. Further, antisense technology combined with gene therapy is useful for example, for suppression of expression of a mutant gene product. Such gene therapy would be most advantageous in combination with a replacement regimen utilizing the "normal" gene to provide a "normal" gene product.

Unfortunately, the effective use of antisense oligonucleotides has been limited due to several problems. Disadvantages include the transient nature of ODNs, and their toxicity and propensity for producing non-sequence specified biological effects. Other disadvantages include low expression or limited stability of complementary RNAs which result in their nonspecific targeting or low efficiency of target inhibition. Antisense oligonucleotides are often poorly taken up by cells and therefore may never reach their target site. Often, antisense oligonucleotides do not reach the nucleus of a cell once administered, the site of their RNA and DNA targets. In certain applications the antisense molecules are microinjected directly into the cells. This technique works well in the laboratory, however, it cannot be applied to patients. Many of the studies with antisense show that gene expression is suppressed by 80–90% of the normal level, however, such reduction is not typically sufficient to reduce the biological effect, e.g., 10–20% expression is sufficient to maintain the biological function sought to suppress.

There is a need to develop a delivery system for antisense molecules that gives the antisense enhanced stability, for example by being resistant to nuclease activity or by being enriched in the nucleus, while still allowing specificity of the antisense for its target RNA or DNA. Such a system would provide effective targeting of the message with the end result being significant inhibition of expression of a particular gene.

SUMMARY OF THE INVENTION

The present invention provides a novel nucleic acid construct for delivery of antisense targeting sequences for inhibition of selected genes in a cell. The construct includes intact stem loop structures and an antisense nucleic acid. This allele-specific targeting is also useful in combination with replacement gene therapy.

In a first embodiment, the invention provides a nucleic acid construct for suppressing gene expression. The construct includes a 5' stem loop structure, an antisense nucleic acid, and a 3' stem loop structure. Such "unmodified" or "intact" stem loop structures flank the antisense nucleic acid so that the antisense oligonucleotides can readily interact with any target sequence. In a preferred embodiment, the stem loop structures are U snRNA stem loops, and most preferably, U1 snRNa stem loops. The construct provides a cloning site outside of the stem loop structures, thus rendering the stem loop structures "unmodified," into which virtually any antisense oligonucleotide could be inserted. In contrast to previous antisense delivery vehicles which have been designed to interfere with mRNA splicing, the construct of the present invention does not necessarily affect the splicing machinery so as not to disrupt normal cellular mRNA processing. In other words, while previous constructs retain elements that interact with spliceosome proteins, the construct of the invention eliminates such elements. Preferably, a U1 snRNA promoter is included in the construct. Optionally, a ribozyme nucleic acid is included in the construct.

In another embodiment, the invention provides a method for suppression of gene expression whereby a suppressive-effective amount of the nucleic acid construct of the invention is administered to a cell thereby suppressing expression of the gene. The method is particularly useful when used in combination with replacement gene therapy which provides a gene which encodes and can reconstitute the wild-type protein and which is resistant to targeting by the antisense and/or ribozyme.

The seminal discovery of the delivery vehicle of the invention now allows transgenic knockout animals to be created for the study of known or as of yet unknown genes. For example, phenotypic consequences of loss of function due to targeted disruption of a gene(s) can be determined.

DESCRIPTION OF THE PREFERRED EMBODIMENTS

The present invention provides a novel nucleic acid construct which provides a general means of delivery for antisense targeting sequences. The construct includes stabilizing structural elements, stem loop structures, which increase the effectiveness of the targeting construct. Also included is a method of suppression of gene expression utilizing the novel construct of the invention.

The nucleic acid construct of the invention which is useful for suppressing gene expression includes 5' and 3' stem loop structures and an antisense nucleic acid. While not wanting to be bound by a particular theory, it is believed that the stem loop structures provide enhanced stability of the targeting molecules by conferring resistance to exonucleases and also promote duplex formation and stability.

The "stem loop" structures refer to nucleic acid structures that have folding patterns which form hairpins and flank the antisense targeting sequence. The stem loop structures are preferably unmodified, naturally occurring structures. Alternatively, one of skill in the art would be able to synthesize such structures to "mimic " the naturally occurring structures. The preferred stem loop structures in the construct of the invention are unmodified U snRNA structures. The term "unmodified" means that the folding pattern of the stem loop structure is not compromised by alterations in the nucleic acid sequence of the naturally occurring molecule. For example, it is understood that alterations which include, but are not limited to, mutations, insertions, deletions and substitutions of one or more nucleotides can be made within the sequence of the stem loop, as long as the stabilization function and hairpin formation of the stem loop is maintained.

Figure 1:
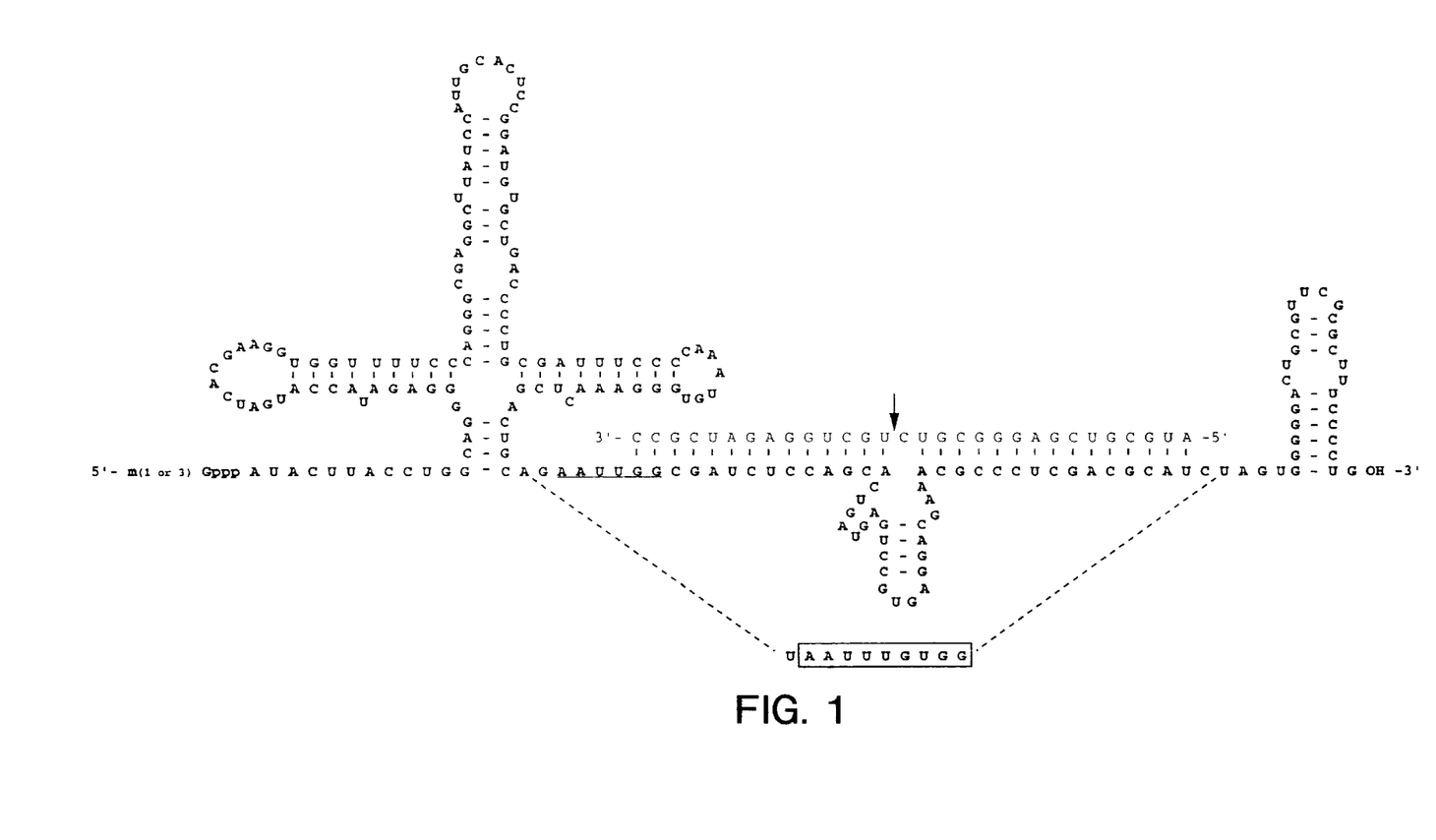
FIG. 1 shows an illustrative expression construct of the invention.

Preferably, the stem loop structures are derived from or synthesized according to the nucleotide sequence of the U snRNA stem loop structures. An exemplary construct utilizing U1 snRNA stem loops is shown in FIG. 1 herein. One can produce a chimeric construct having a 5' stem loop structure from one species and a 3' structure from a second species. For example, a 5' stem loop is derived from human U snRNA and the 3' stem loop derived from a yeast U snRNA. Other snRNA stem loop structures can be derived from other mammals (e.g., porcine, bovine), or yeast for example. Other chimeric constructs can be prepared using a 5' stem loop structure from one snRNA (e.g., U1) and a 3' stem loop structure from another snRNA (e.g., U3). Virtually any combination of stem loop structures is envisioned in the construct of the invention.

As used herein, the term "nucleic acid" or nucleic acid sequence" refers to a polymer of deoxyribonucleotides or ribonucleotides, in the form of a separate fragment or as a component of a larger construct. For example, nucleic acids can be assembled from cDNA fragments or from oligonucleotides to generate a synthetic gene which is capable of being expressed in a recombinant transcriptional unit. Polynucleotide or nucleic acid sequences of the invention include DNA, RNA and cDNA sequences.

Nucleic acid sequences utilized in the invention can be obtained by several methods. Sequences for specific genes or stem loop structures can determined from published sequences and can also be found in GenBank, National Institutes of Health computer database. Nucleic acids can then be chemically synthesized by standard methods for example.

The construct of the invention includes an antisense nucleic acid flanked by the stem loop structures. The antisense nucleic acid can be directed toward any target nucleic acid, and preferably to a target message (mRNA). Any antisense which includes sequences capable of hybridizing with its complementary target can be used in the construct of the invention. For example, antisense sequences can be directed to the 5' or 3' termini of the target message, to splice junctions, or to internal sequences. One of skill in the art will readily be able to determine which sequences to use as the appropriate antisense nucleic acid construct. "Antisense nucleic acids" are DNA or RNA molecules that are complementary to at least a portion of a specific mRNA molecule (Weintraub, Scientific American, 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to be toxic than larger molecules when introduced into the target cell. The use of antisense methods to inhibit the in vitro translation of genes is well known in the art (Marcus-Sakura, Anal.Biochem., 172:289, 1988). An antisense core nucleic acid may contain about 10 nucleotides complementary to the target message. Examples of target messages include transcription regulatory factors (e.g., rent-1), viral encoded proteins (e.g., human papilloma virus E6, human immunodeficiency virus tat), (e.g., haluronic acid synthase), structural proteins (e.g., fibrillin), cytokines, oncogenes and growth factors (e.g., interleukins), etc. It should be noted that the antisense nucleic acid can be useful for reducing the expression of either normal or aberrant genes.

The antisense nucleic acid can be used to block expression of a mutant protein or a dominantly active gene product, such as amyloid precursor protein that accumulates in Alzheimer's disease. Such methods are also useful for the treatment of Huntington's disease, hereditary Parkinsonism, and other diseases. Antisense nucleic acids are also useful for the inhibition of expression of proteins associated with toxicity or gene products introduced into the cell, such as those introduced by an infectious agent (e.g., a virus).

It may be desirable to transfer an antisense nucleic acid encoding a biological response modifier in order to reduce the expression of such biological response modifier. Included in this category are nucleic acids encoding immunopotentiating agents including a number of the cytokines classified as "interleukins". These include, for example, interleukins 1 through 12. Also included in this category, although not necessarily working according to the same mechanisms, are interferons, and in particular gamma interferon (γ-IFN), tumor necrosis factor (TNF) and granulocyte-macrophage-colony stimulating factor (GM-CSF). It may be desirable to deliver such antisense nucleic acids to cells of the immune system to treat enzymatic related disorders or immune defects. Antisense nucleic acids can be used to reduce expression of growth factors, toxic peptides, ligands, receptors, or other physiologically important proteins.

The construct of the invention may further include a ribozyme nucleic acid. Ribozymes are RNA molecules possessing the ability to specifically cleave other single-stranded RNA. Through the modification of nucleotide sequences which encode these RNAs, it is possible to engineer molecules that recognize specific nucleotide sequences in an RNA molecule and cleave it (Cech, *J. Amer. Med. Assn.*, 260:3030, 1988). A major advantage of this approach is that, because the ribozymes are engineered to be sequence-specific, only mRNAs with sequences complementary to the construct containing the ribozyme are inactivated.

There are two basic types of ribozymes namely, tetrahymena-type (Hasselhoff, et al., *Nature*, 334:585, 1988) and "hammerhead"-type. Tetrahymena-type ribozymes recognize sequences which are four bases in length, while "hammerhead"-type ribozymes recognize base sequences from about 3 to 18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species. The preferred ribozyme of the present invention is a hammerhead type ribozyme. The target message is required to contain a ribozyme cleavage site sequence such as 5'-GUC-3' or 5'-GUA-3' when a ribozyme is included in the construct.

The construct may also optionally include a triplex oligomer. Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., *Antisense Res. and Dev.*, 1(3):227, 1991; Helene, C., *Anticancer Drug Design*, 6(6):569, 1991).

The phrase "nucleic acid sequence expressing a product of interest" refers to a nucleic acid sequence which when expressed results in a product selected from a protein or antisense RNA, for example. The term "structural gene" excludes the non-coding regulatory sequence which drives transcription. The structural gene may be derived in whole or in part from any source known to the art, including a plant, a fungus, an animal, a bacterial genome or episome, eukaryotic, nuclear or plasmid DNA, cDNA, viral DNA or chemically synthesized DNA. A structural gene may contain one or more modifications in either the coding or the untranslated regions which could affect the biological activity or the chemical structure of the expression product, the rate of expression or the manner of expression control. Such modifications include, but are not limited to, mutations, insertions, deletions and substitutions of one or more nucleotides. The structural gene may constitute an uninterrupted coding sequence or it may include one or more introns, bound by the appropriate splice junctions.

The term "operably associated" refers to functional linkage between the regulatory (e.g., promoter) sequence and the nucleic acid regulated by the regulatory sequence. The operably linked regulatory sequence controls the expression of the product expressed by the structural gene or antisense. The regulatory sequence may be homologous or heterologous to the desired gene sequence. A wide range of promoters may be utilized, including viral or mammalian promoters. Cell- or tissue-specific promoters can be utilized to target expression of gene sequences in specific cell populations. Suitable mammalian and viral promoters for the present invention are available in the art. A preferred promoter in the construct of the invention is a U snRNA promoter, and most preferably, a U1 snRNA promoter.

The choice of a particular heterologous promoter region as a "regulatory nucleotide sequence" of the invention, is dictated by the spatial and temporal pattern of expression that is desired for the transactivator gene and ultimately for the target transgene. Promoter regions of the invention include eukaryotically derived promoters which predominantly direct expression in, for example, the reproductive system (e.g., breast, ovary, testes); the musculoskeletal system (e.g., muscle or joint tissue); the cardiovascular system (e.g., capillaries or heart); the respiratory system (e.g., lung or nasal passages); the urological system (e.g., kidney or bladder); the gastrointestinal system (e.g., pancreas, liver, or intestines); the immune system (e.g., thymus, spleen, or circulating immunological cells); the endocrine system (e.g., pituitary, gonads, and thyroid); the nervous system (e.g., neurons); and the hematopoietic system (e.g., bone marrow and peripheral blood). Further, promoters of the invention include, but are not limited to the elastase promoter (including its enhancer; expression in pancreatic acinar cells); the alpha-A-crystallin promoter (expression in the eye lens tissue); the insulin promoter (including enhancer; expression in the pancreatic beta cells) and the albumin promoter region, including its enhancer.

Alternatively, non-eukaryotically-derived promoters such as virally-derived and prokaryotically-derived promoters are also included in the present invention. Such virally-derived promoters include, but are not limited to MMTV and MoSV LTR, SV40 early region, RSV or CMV LTR, which direct expression of viral or host genes in specific tissues and in many cell types.

Promoters useful in the invention include both constitutive and inducible natural promoters as well as engineered promoters. To be most useful, an inducible promoter should 1) provide low expression in the absence of the inducer; 2) provide high expression in the presence of the inducer; 3) use an induction scheme that does not interfere with the normal physiology of the cell; and 4) have no effect on the expression of other genes. Both constitutive and inducible promoters and enhancers will be known to those of skill in the art. The promoters used in the construct of the present invention may be modified, if desired, to affect their control characteristics.

The regulatory nucleotide sequence of the invention may also include "enhancer" regions. Enhancers, as used herein, refer to DNA sequences which affect transcription of a gene by RNA polymerase II, without regard to position or orientation. An enhancer region can be thousands of base pairs from a transcription unit and still affect its transcription. Example of enhancers known in the art include the immunoglobulin heavy (mu) chain or light (kappa) chain enhancers and the SV40 72-base pair repeats.

It may be desirable to deliver the construct of the invention directly to the cell without the requirement for expression, therefore, a promoter or other regulatory nucleic acid is optional. One example of a targeted delivery system for antisense polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes or liposome formulations. The preferred colloidal system of this invention is a liposome. Liposomes are artificial membrane vesicles which are useful as delivery vehicles in vitro and in vivo. These formulations may have net cationic, anionic or neutral charge characteristics are useful characteristics with in vitro, in vivo and ex vivo delivery methods. It has been shown that large unilamellar vesicles (LUV), which range in size from 0.2–4.0 μm can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques*, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

The construct of the invention can also be delivered as a naked "gene expression vector". This means that the construct is not associated with a delivery vehicle (e.g., liposomes, colloidal particles and the like). One of the principal advantages touted for naked DNA vectors has been the lack of immune responses stimulated by the vector itself.

The backbone or framework of the construct preferably includes U1 snRNA nucleic acid sequences since U1 snRNA is enriched in the nucleus, is widely dispersed in the nucleoplasm, and is abundantly expressed. In the exemplary construct shown in FIG. 1, an "antisense targeting core" was substituted for the Sm protein binding site between the two naturally occurring U1 snRNA hairpins. This core contains a 30–35 basepair sequence that is directly complementary to the target message, interrupted in its center by an autocatalytic hammerhead ribozyme loop. Duplex formation aligns the ribozyme with the GUC or GUA consensus sites for ribozyme cleavage within the target message. An illustrative expression construct of the invention which targets RENT1 transcripts, which are involved in the NMRD pathway, described below, is shown in FIG. 1. The term rent1 and RENT1 (regulator of nonsense transcripts) refers to the gene and protein, respectively, from either the murine or human species.

The construct described above is useful for suppressing gene expression. For example, it may be desirable to modulate the expression of a gene when it is over-expressed. Where a cell proliferative disorder is associated with the expression of a gene, nucleic acid sequences that interfere with the gene's expression at the translational level can be used. This approach utilizes, for example, antisense nucleic acid, ribozymes, or triplex agents to block transcription or translation of a specific mRNA, either by masking that mRNA with an antisense nucleic acid or triplex agent, or by cleaving it with a ribozyme, as described above.

The construct may also optionally include a 5' cap structure, such as a trimethylguanosine cap.

In another embodiment, the present invention also includes a method for suppression of gene expression which includes administering to a cell a suppressive-effective amount of the nucleic acid construct of the invention so that the expression of the gene is suppressed. The term "suppressive-effective" amount means that amount of the construct, and thus antisense, administered is sufficient to suppress the expression of the target, e.g., inhibit translation of mRNA, by at least 75% of the normal expression, and preferably by at least 90%. The effectiveness of the construct can be determined phenotypically or by standard Northern blot analysis or immunohistochemically, for example. Other standard nucleic acid detection techniques or alternatively immunodiagnostic techniques will be known to those of skill in the art (e.g., Western or Northwestern blot analysis).

The present invention also provides a method of gene therapy for the treatment of cell proliferative or immunologic disorders and diseases such as which are mediated by various proteins. The term "cell-proliferative disorder" denotes malignant as well as non-malignant cell populations which often appear to differ from the surrounding tissue both morphologically and genotypically. Such disorders may be associated, for example, with abnormal expression of a gene. "Abnormal expression" encompasses both increased or decreased levels of expression, as well as expression of a mutant form of a gene such that the normal function of the gene product is altered. Abnormal expression also includes inappropriate expression of during the cell cycle or in an incorrect cell type. The antisense polynucleotide is useful in treating malignancies of the various organ systems. Such therapy would achieve its therapeutic effect by introduction of the antisense construct into cells having the proliferative disorder. Delivery of antisense polynucleotide, can be achieved using a recombinant expression vector such as a chimeric virus or a colloidal dispersion system as described above.

The construct may also be useful in treating malignancies of the various organ systems, such as, for example, lung, breast, lymphoid, gastrointestinal, and genito-urinary tract as well as adenocarcinomas which include malignancies such as most colon cancers, renal-cell carcinoma, prostate cancer, leukemia, breast cancer, non-small cell carcinoma of the lung, cancer of the small intestine, and cancer of the esophagus.

The method is also useful in treating non-malignant or immunologically-related cell-proliferative diseases such as psoriasis, pemphigus vulgaris, Bechet's syndrome, acute respiratory distress syndrome (ARDS), ischemic heart disease, post-dialysis syndrome, rheumatoid arthritis, acquired immune deficiency syndrome, vasculitis, lipid histiocytosis, septic shock and inflammation in general.

Various viral vectors which can be utilized for gene therapy as taught herein include adenovirus, adeno-associated virus, herpes virus, vaccinia, or, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). Preferably, when the subject is a human, a vector such as the gibbon ape leukemia virus (GaLV) is utilized. A number of additional retroviral vectors can incorporate multiple genes. All of these vectors can transfer or incorporate a gene for a selectable marker so that transduced cells can be identified and generated. By inserting a sequence of interest into the viral vector, along with another gene which encodes the ligand for a receptor on a specific target cell, for example, the vector is now target specific. Retroviral vectors can be made target specific by attaching, for example, a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome or attached to a viral envelope to allow target specific delivery of the retroviral vector containing the antisense polynucleotide.

Administration of the construct of the invention can be in vivo, in vitro or ex vivo.

The method of the invention also envisions gene replacement therapy to reconstitute expression of a wild-type protein in cells expressing a defective protein or, in the cae of a heterozygote, a defective and a "normal" protein. Therefore, in another embodiment the invention provides a method of suppressing gene expression as above and further comprises administering a modified nucleic acid encoding a wild-type polypeptide corresponding to the gene product of the gene being suppressed, wherein the modified nucleic acid is resistant to ribozyme cleavage and/or antisense inhibition. Due to degeneracy in the genetic code, multiple nucleotide substitutions can be made across the antisense oligonucleotide target region of the coding sequence within an exogenously supplied expression construct encoding the wild-type gene of interest. Such substitutions would inhibit duplex formation between the gene suppressed and the antisense nucleic acid and transcripts derived from the replacement "normal" gene, while maintaining the fidelity of the amino acid sequence. In other words, the replacement gene would provide a protein with the correct amino acid sequence utilizing codons with nucleotides that are not recognized by the antisense construct and/or ribozyme. In this method, it is therefore possible to "knockout" a defective copy of a gene/mRNA and introduce a "normal" copy resistant to the "knockout" construct. Thus, both normal and aberrant expression of a gene can be blocked by introduction of the antisense construct of the invention; to restore normal function of the gene, a copy of the wild-type gene is introduced, that, while coding for a normal protein, is resistant to duplex formation with the antisense construct and/or ribozyme cleavage.

There are a number of inherited diseases in which defective genes may be replaced including: lysosomal storage diseases such as those involving β-hexosaminidase or glucocerebrosidase; deficiencies in hypoxanthine phosphoribosyl transferase activity (the "Lesch-Nyhan" syndrome); amyloid polyneuropathies (prealbumin); Duchenne's muscular dystrophy, and retinoblastoma, for example.

Pathologic disorders that can be targeted using the method of the invention include but are not limited to viral infections, inflammatory disorders, cardiovascular disease, cancers, genetic disorders and autoimmune diseases.

The method of the present invention is also useful for suppression of a dominant negative mutation. The term "dominant negative" is a term of art and refers to expression of a gene resulting in a gene product that actively interferes with the function of a "normal", endogenous protein. Thus, a mutant protein or dominantly active gene product, such as amyloid precursor protein that accumulates in Alzheimer's disease can be blocked. The dominant negative phenotype is conveyed by the expression of the mutant protein that interferes with the function of the normal protein. Such an effect is similar to the effect of dominance of one allele of a pair of alleles encoding homologous genes on a pair of homologous chromosomes such that the phenotypic effect of the one allele exerts a deleterious controlling influence over the other allele.

The nucleic acid construct can be utilized in the discovery of unknown human genes, for example, with a priori knowledge of the gene in question. In one embodiment of this invention, cells are isolated from an individual displaying a particular phenotype which is suspected of being caused by a gene or genes containing nonsense mutations. A subset of these cells is contacted (e.g. by transfecting the cells), with the construct that contains at least an antisense nucleic acid for suppression or inhibition of the expression or function of a gene (e.g., Rent-1 gene or other genes involved in NMRD) or its gene product in the cells. Levels of mRNA containing nonsense mutations in these cells are elevated to higher levels. Using standard techniques of differential display of mRNA, or genetic subtraction techniques commonly applied to cDNAs, the mRNA containing nonsense mutations can be enriched and then isolated by comparing the mRNA populations of the original cells with the mRNA populations in cells containing the antisense.

In a further embodiment, a transgenic animal can be developed using the novel construct and method of the invention in order to identify the impact of increased or decreased gene expression on a particular pathway or phenotype. Protocols useful in producing such transgenic animals are described below. The protocol generally follows conventional techniques for introduction of expressible transgenes into mammals. Those of ordinary skill in the art will be familiar with these applications and will be able to apply the techniques in the context of the present invention without undue experimentation.

For example, embryonic target cells at various developmental stages can be used to introduce transgenes. Different methods are used depending on the stage of development of the embryonic target cell. The zygote is the best target for microinjection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster, et al, *Proc. Natl. Acad. Sci. USA* 82:4438–4442, 1985). As a consequence, all cells of the transgenic non-human animal will carry the incorporated transgene. In general, this will also be reflected in the efficient transmission of the transgene to offspring of the founder since 50% of the germ cells will harbor the transgene. Microinjection of zygotes is a preferred method for incorporating transgenes in practicing the invention.

Retroviral infection can also be used to introduce transgene into a non-human animal. The developing non-human embryo can be cultured in vitro to the blastocyst stage. During this time, the blastomeres can be targets for retroviral infection (Jaenisch, *Proc. Natl. Acad. Sci USA* 73:1260–1264, 1976). Efficient infection of the blastomeres is obtained by enzymatic treatment to remove the zona pellucida (Hogan, et al., *Manipulating the Mouse Embryo*, Cold Spring Harbor Laboratory Press, Cold Spring Harbor, N.Y., 1986). The viral vector system used to introduce the transgene is typically a replication-defective retrovirus carrying the transgene (Jahner, et al., *Proc. Natl. Acad. Sci. USA*, 82:6927–6931, 1985; Van der Putten, et al., *Proc. Natl Acad. Sci USA* 82:6148–6152). Transfection is easily and efficiently obtained by culturing the blastomeres on a monolayer of virus-producing cells (Van der Putten, supra; Steward, et al., *EMBO J.*, 6:383–388, 1987).

Alternatively, infection can be performed at a later stage. Virus or virus-producing cells can be injected into the blastocoele (Jahner, et al., *Nature*, 298:623–628, 1982). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line, albeit with low efficiency, by intrauterine retroviral infection of the midgestation embryo (Jahner, et al., supra, 1982).

A third type of target cell for introduction of heterologous nucleic acid sequences is the embryonal stem cell (ES). ES cells are obtained from pre-implantation embryos cultured in vitro and fused with embryos (Evans, et al., Nature, 292:154–156, 1981; Bradley, et al., Nature, 309:255–258, 1984; Gossler, et al., Proc. Natl. Acad. Sci USA, 83:9065–9069, 1986; and Robertson, et al., Nature, 322:445–448, 1986). Transgenes can be efficiently introduced into the ES cells by DNA transfection or by retrovirus-mediated transduction. These transformed ES cells can thereafter be combined with blastocysts from a non-human animal. The ES cells will thereafter colonize the embryo and contribute to the germ line of the resulting chimeric animal (see for review, Jaenisch, Science, 240:1468–1474, 1988). Any ES cell may be used in accordance with the present invention. It is, however, preferred to use primary isolates of ES cells. Such isolates may be obtained directly from embryos such as with the CCE cell line disclosed by Robertson, E. J., in Current Communications in Molecular biology, Capecchi,M. R. (Ed.) Cold Springs Harbor Press, Cold Springs Harbor, N.Y. (1989), pp.39–44), or from the clonal isolation of ES cells from the CCE cell line (Schwartzberg, P. A. et al., Science 246:799 (1989). ES cells may be derived or isolated from any species, although cells derived or isolated from mammals such as rodents, rabbits, and non-human primates are preferred.

Construction of transgenes can be performed by those of ordinary skill in the art using the teachings herein. One of ordinary skill in the art can "knock out" a gene in mice by targeted disruption of the gene. This can be accomplished by homologous recombination in murine embryonic stem (ES) cells using standard techniques. The clinical and cellular consequences of targeted disruption can be investigated in multiple genetic backgrounds including inbred strains, strains with many undefined nonsense alleles, and strains of known mutant genotype to determine if: (a) targeted disruption of the gene can effect a loss of function; (b) loss of function can have an phenotype consequences (i.e., the creation of knockout phenotypes), (c) loss of the gene product unmasks the effects of protein that can be expressed from "physiologic" somatically acquired or inherited nonsense alleles upon transcript stabilization.

The cre/lox system as described in U.S. patent Ser. No. 4,959,317, incorporated herein by reference, can be utilized in the production of transgenic animals. A first and second loxP DNA sequence is introduced into cells connected by a pre-selected antisense or replacement gene, herein referred to as a "target transgene". The "target transgene" of interest can be a complete gene or any other sequence of nucleotides including those of homologous, heterologous, or synthetic origin. The target transgene sequence can be for example, an antisense or replacement gene for a structural protein, an enzyme, or a regulatory molecule. The target transgene may also be a gene of undetermined function. Using tissue-specific or developmentally-specific regulatory sequences (as described above) to direct expression of the target transgene, a function could be identified. If the first and second lox sites have the same orientation (direct repeats), activation of the regulatory nucleotide sequence of the transactivator transgene results in a deletion of the target transgene DNA, such that ablation or modification of activity results. If the first and second lox sites have opposite orientation (inverted repeats), activation of the regulatory nucleotide produces an inversion of the nucleotides sequence of the target transgene.

The construct of the invention may be used to introduce DNA sequences into the germ line cells of "non-humans" to create transgenic animals. The preferred animal of the invention is a mouse. However, other non-humans of the invention include but are not limited to other rodents (e.g. rat, hamster), rabbits, chickens, sheep, goats, fish, pigs, cattle, and non-human primates.

In yet another embodiment, an antisense library can be constructed using the nucleic acid construct of the invention in order to identify novel genes. For example, a U1 construct library containing antisense core sequences (e.g., random sequences or sequences derived from a cDNA library) is transfected into host cells and clones exhibiting a desired phenotype are identified. Such clones are then examined to determine the nature of the regulatory sequence in the construct. Therefore, novel genes having specific functions can be identified. For example, cells that acquire a transformed phenotype may contain an antisense molecule for a novel tumor suppressor gene. A match between a given suppressive nucleic acid and a previously cloned gene can be made using standard techniques (e.g., BLAST search algorithm).

The following Examples are intended to illustrate, but not to limit the invention. While such Examples are typical of those that might be used, other procedures known to those skilled in the art may alternatively be utilized.

EXAMPLES

The following examples provide a description of construction of an exemplary nucleic acid construct of the invention, utilizing 5' and 3' unmodified stem loop structures from U1 snRNA which flank an antisense molecule directed toward the fibrillin-1 gene (mRNA).

Example 1

An antisense expression construct was constructed that incorporates several potentially enhancing features. The pU1/FIB vector was constructed on the backbone of the pZeoSV (Invitrogen) prokaryotic/eukaryotic expression vector. The SV40 promoter, polyadenylation site and polylinker were excised from pZeoSV at the BamHI sites. A U1 snRNA expression cassette cloned into pUC13 was excised with BamHI digestion and ligated into the BamHI sites of the modified pZeoSV. Two rounds of site-directed mutagenesis (Deng, et al., Anal. Biochem., 200, 81; 1992) were then performed to change four nucleotides flanking the Sm protein restriction sites (pZeoU1EcoSpe). Complementary oligonucleotides that encode the antisense 'core' sequence, shown in FIG. 1, including the 24 highly conserved nucleotides of hammerhead ribozymes (Cech, et al., Ann. Rev. Biochem., 55:599, were synthesized and annealed at 40° C. such that the remaining 5' and 3' overhangs were exactly complementary to the overhangs left by EcoRI and SpeI digestion. The sequences of the oligonucleotides were as follows:
5'-AATTGGCGATCTCCAGCACTGATGAGTCCGTGAGG ACGAAACGCCCTCGACGCAT-3' (SEQ ID NO:1),
5'-CTAGATGCGTCGAGGGCGTTTCGTCCTCACGGACTC ATCAGTGCTGGAGATCGCC-3' (SEQ ID NO:2) (sense and antisense, respectively).
The resulting duplex was ligated into the EcoRI and SpeI sites of pZeoU1EcoSpe to create pU1FIB. All ligation junctions were sequenced to verify the identity and orientation of the insert.

In that the structure described for naturally occurring antisense RNAs is highly similar to that for small nuclear RNAs (snRNAs), essential components of the spliceosome complex that are abundant and stable in the nucleus of mammalian cells, the U1 snRNA gene was selected as the framework for vector construction (Guthrie, et al., *Annu. Rev. Genet.*, 22; 387, 1988). Other attributes include the potent and constitutively active nature of the U1 snRNA promoter, the ability of the unusual trimethylguanosine 5' cap and Sm protein interactions to signal transport of U1 snRNA back into the nucleus (Hamm, et al., *Cell*, 62; 569, 1990; Fischer, et al., *Science* 249; 786, 1990; Fischer, et al., *J. Cell Biol.* 113 Mo; 705, 1991; Plessel, et al., *Mol. Cell. Biol.* 14, 4160,1994), and the lack of polyadenylation of mature snRNAs, a factor which may favorably influence transcript trafficking and localization (Zhong, et al., *Proc. Natl. Acad. Sci. USA*, 91; 4258, 1994). Moreover, unlike other spliceosome components, U1 snRNA is widely dispersed in the nucleoplasm (Carmo-Fonseca, et al., *EMBO J.*, 10; 195, 1991; Matera, et al., *J. Cell Biol.*, 121; 715, 1993).

As an illustrative example, the antisense targeting 'core' was designed to contain sequences exactly complementary to coding nucleotides 1–15 and 17–30 of fibrillin mRNA (Corson, et al., *Genomics*, 17; 476, 1993; Pereira, et al., *Hum. Mol. Genet.*, 2; 961, 1993) separated by the 22 bp hammerhead ribozyme loop. Dominant-negative forms of fibrillin-1 cause Marfan syndrome, an autosomal dominant systemic disorder of connective tissue (Dietz, et al., *Nature*, 352; 337, 1991). The regions of complementarity were predicted to align the autocatalytic structure with the consensus sequence for ribozyme cleavage (5'-GUC-3') within the target message (Cech, et al., *Annu. Rev. Biochem.*, 55; 599, 1986; T. R. Cech, *Science*, 236; 1532, 1987; T. R. Cech, *Ann. Rev. Biochem*, 59, 543, 1990; Haseloff, et al., *Nature*, 334; 585, 1988). This antisense targeting sequence was substituted for the short Sm protein binding sequence between the two hairpin loops of U1 snRNA (Guthrie, *Annu. Rev. Genet.*, 22; 387, 1988.) The sequence of the resulting chimeric RNA (FIG. 1) was analyzed using a program that predicts RNA structure (Mike Zuker's RNA page: http://ibc.wustl.edu/~zuker/rna/). The boundaries of the targeting sequence utilized in the construct were selected to maximize preservation of the U1 snRNA stem-loops, the ribozyme secondary structure and the accessibility of the sequence complementary to the target message. Expression of the chimeric RNA was under the transcriptional control of a region of U1 snRNA 5'-flanking sequence that has been shown to be potent and constitutively active (Zhuang, et al., *Cell*, 46; 827, 1986; Maugin, et al., *EMBO J.*, 5, 987, 1986); and Asselbeyers, et al., *Mol. Biol. Rep.* 17; 101, 1993).

Figure 2:
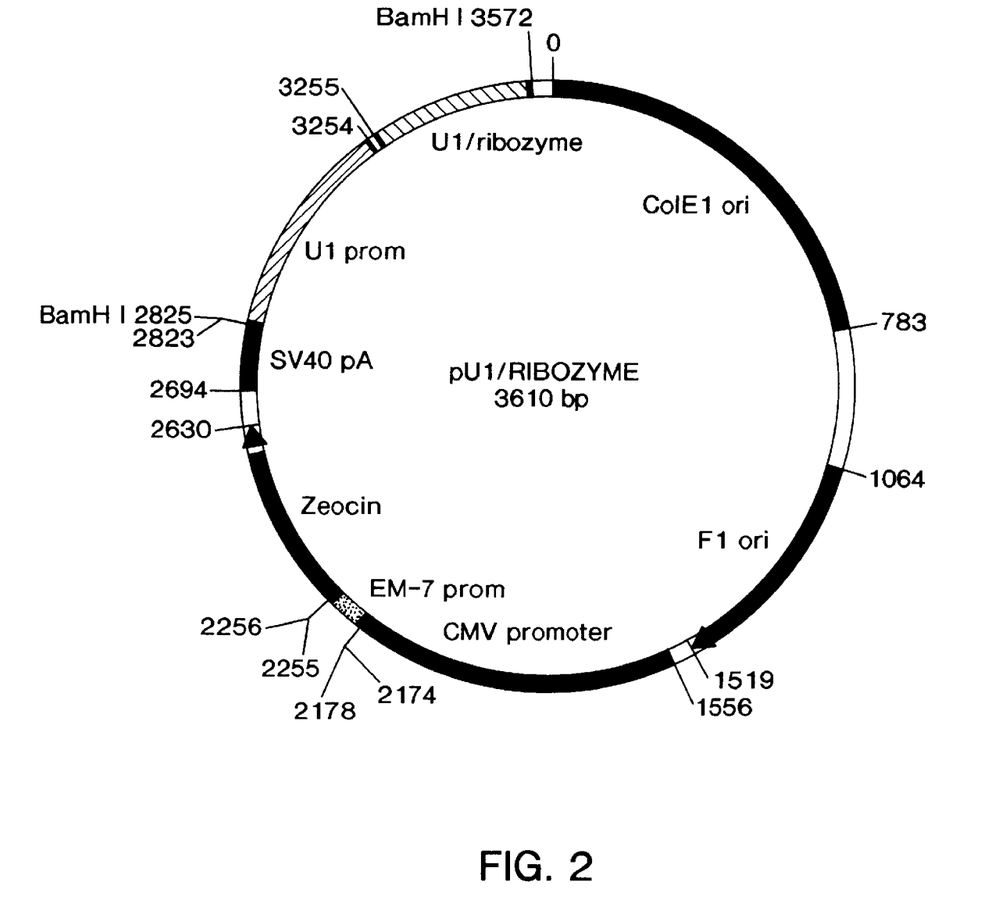
FIG. 2 shows the sequence and predicted structure of chimeric transcripts derived from pU1/FIB.
Figure 3A:
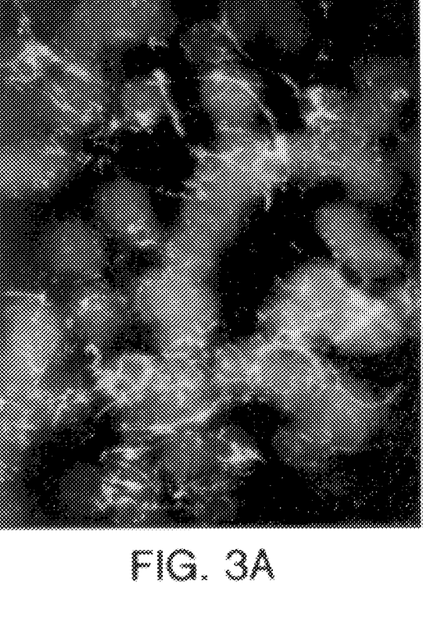
FIG. 3A–3D shows an immunohistochemical analysis of MG63 cells that were stably transfected with an expression construct (pZeoSVLacZ, Invitrogen) lacking targeting sequence (panels A and C) or pU1/FIB (panels B and D).
Figure 3B:
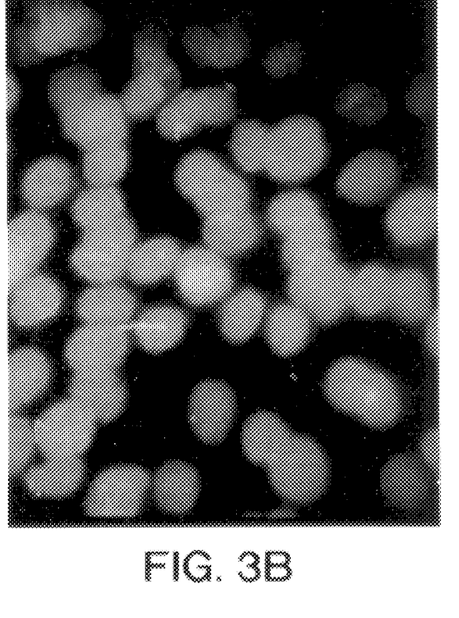
Figure 3C:
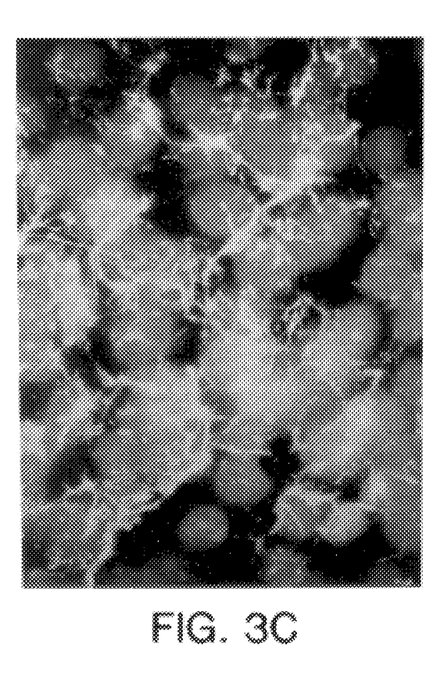
Figure 3D:
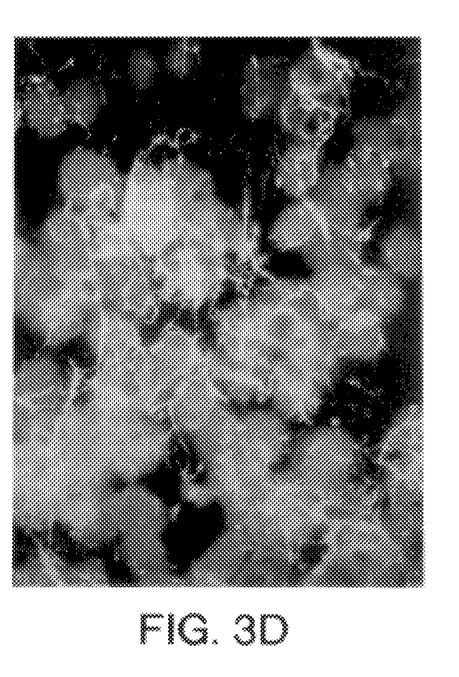

FIG. 2 shows the sequence and predicted structure of chimeric transcripts derived from pU1/FIB. The Sm protein binding site of U1 snRNA (boxed) has been substituted by an antisense targeting core (flanked by dashed lines) that is complementary to the first 30 coding nucleotides of FBN1 and contains a hammerhead ribozyme sequence in its center. The two stem-loop structures of U1 snRNA are maintained. Cleavage of the target message (unbolded characters) is predicted to occur immediately following the consensus sequence 5'-GUC-3' (arrow). The 5' cap structure of the chimeric targeting molecule may contain 1 or 3 methyl (m) groups. A sequence in the chimeric molecule (5'-AAUUGG-3', underlined) remains highly similar to the consensus for Sm protein binding, PuA(U)nGPu (Pu=A or G).

A human osteosarcoma (MG63) cell line was stably transfected with either a reporter gene expression vector (pZeoSVLacZ, Invitrogen) or the chimeric construct (pU1/FIB) by long-term selection for zeomycin resistance. Human osteosarcoma (MG63) cells (Sakai, et al., *J Cell Biol.*, 103; 2499, 1986) were grown to 60% confluency and transfected with either linearized pU1/FIB or a lac Z reporter gene construct (pZeoSVLacZ, Invitrogen), used as a control. The transfections were performed using a DOTAP liposome formulation (Boehringer Mannheim, 1 mg/ml) according to manufacturer's instructions. Cells were grown in MEM media (Cellgro) with 10% FCS and 250 µg/ml of zeocin (Invitrogen), and were maintained in selection for 14 days prior to the isolation of clonal colonies. Mono- and polyclonal colonies were established and grown to confluency.

FIG. 3 shows an immunohistochemical analysis of MG63 cells that were stably transfected with an expression construct (pZeoSVLacZ, Invitrogen) lacking targeting sequence (panels A and C) or pU1/FIB (panels B and D). The antibodies either recognized epitopes in fibrillin-1 (A and B) or fibronectin (C and D). Analysis was performed in duplicate for each of three independent clonal colonies for each construct, with identical results. Representative fields are shown at 63× magnification. Untransfected MG63 cells showed a pattern of protein deposition that was indistinguishable from that for cells transfected with pZeoSVLacZ.

Fibrillin-1 was strikingly absent upon immunohistochemical analysis (Eldadah et al., *J. Clin. Invest.*, 95; 874, 1995) using either anti-fibrillin-1 mAb 69 (a gift from L. Y. Sakai) or an anti-fibronection mAb (Sigma) of cells harboring pU1/FIB, while cells transfected with pZeoSVLacZ showed a pattern of protein deposition that was indistinguishable from untransfected controls (FIG. 3). The lines harboring pU1/FIB could not be distinguished from mock-transfected or untransfected cells upon immunohistochemical analysis with a monoclonal antibody to fibronectin, suggesting specificity for the targeting process.

Antisense RNAs expressed by pU1/FIB might inhibit fibrillin-1 expression by multiple mechanisms. Ribozyme cleavage would remove the 5' cap from targeted transcripts, an event predicted to effect their rapid degradation. Alternatively, in the absence of ribozyme cleavage, involvement of the initiating AUG codon in duplex formation would impair translation.

The magnetic porous glass direct mRNA purification technique was used to isolate poly(A) RNA (according to the manufacturer's instructions, CPG, Inc.) and Northern blot analyses were performed. Electrophoresis of 3.5 µg of mRNA was performed under denaturing conditions, as previously described (Lehrach, et al., *Biochemistry*, 16; 4743, 1977; D. A. Goldberg, *Proc. Natl. Acad. Sci. USA*, 77; 5794, 1980). The gel was exposed to 60 mjoules UV light to facilitate transfer of large mRNA species. RNA was transferred to nylon membrane using the turboblotting system according to manufacturer's instructions (Schleicher & Schuell). The membrane was washed briefly in 2× SSC, crosslinked with 125 mjoules of UV light and prehybridized in Expresshyb (Clontech) for ½ hour at 68° C. Human cDNA probes encoding fibrillin-1 (nt 370–1183), β-actin (Clontech), and G3PDH (Clontech) were labeled by random priming (Feinberg, et al., *Anal. Biochem.*, 132; 6, 1983). The membrane was hybridized for 1 hour at 68° C., washed first in 2× SSC with 0.05% SDS at room temperature and then in 0.1× SSC with 0.1% SDS at 5° C.

Figure 4:
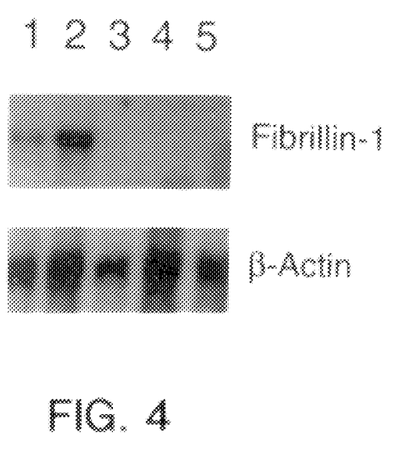
FIG. 4 shows a Northern blot analysis of 3.5 μg of poly(a) RNA extracted from confluent MG63 cells that were untransfected (lane 1), or stably transfected with either pZeoSVLacZ (Lane 2) or pU1/FIB (lane 3–5).

FIG. 4 shows a Northern blot analysis of 3.5 µg of poly(a) RNA extracted from confluent MG63 cells that were untransfected (lane 1), or stably transfected with either pZeoSVLacZ (Lane 2) or pU1/FIB (lane 3–5). Cells for lanes 1 and 3 were polyclonal, while cells for lanes 2, 4 and 5 were derived from monoclonal colonies. Hybridization was performed with radiolabeled cDNA probes complementary to fibrillin-1, β-actin, and G3PDH transcripts.

Northern blot analysis of multiple clonal colonies harboring pU1/FIB revealed undetectable levels of FBN1 message (FIG. 4). FBN1 transcripts were easily detected upon Northern analysis of RNA extracted from untransfected and mock-transfected cells. All cell types showed comparable amounts of β-actin and G3PDH RNA, confirming the specificity of targeting.

A similar U1 construct was created containing U1 snRNA stemloop structures and an antisense core aimed at inhibiting rent-1 expression. Functional analysis of transfected cells showed a significant up-regulation of the steady-state abundance of transcripts derived from endogenous nonsense alleles.

SUMMARY

These data suggest that most, if not all of the inhibitory effect was achieved at the level of target message abundance, presumably by reducing mRNA stability. Although an influence upon transcriptional efficiency cannot be excluded, it is not intuitive given the site and nature of the predicted targeting sequence-target interaction. Based upon previous studies, the antisense-induced mRNA degradation most likely takes place within the nucleus (Murray, et al., in *Modern Cell Biology*, J. A. H. Murray, Ed. (Wiley/Liss, New York, 1992), pp 1–49 M. Cornelissen, *Nucleic Acids Res.*, 17; 7203, 1989.). Three elements of nuclear pre-U1 RNA, the 5' m7G cap, the 3' terminal stem loop, and sequences in the 5'-terminal 124 nucleotides, contribute to the stability of pre-U1 and snRNA and to efficient nuclear export (Neuman de Vegvar, et al., *Mol. Cell. Biol*, 10; 3365, 1990; Terns, et al., *Genes Dev.*, 7; 1898, 1993; Yuo, et al., ibid., 3; 697, 1989; Izaurralde, et al, *Nature*, 376; 709, 1995). Nuclear targeting of cytoplasmic U1 snRNA is influenced by hypermethylation of the 5' cap structure and binding of at least one common U snRNP protein, both dependent upon the integrity of the Sm protein binding site which has been altered in pU1/FIB (Guthrie, et al., *Annu. Rev. Genet.*, 22; 387, 1988). A sequence at the 5' end of the insert (AAUUGG) is highly similar to the consensus site [PuA(U)nGPu, Pu=A or G] for Sm protein binding (Jones, et al., *EMBO J.*, 9; 2555, 1990.). It has also been shown that Sm binding sites are highly tolerant of mutations including internal nucleotide substitutions and deletions (Jones, et al., supra).

Stable transfectin of cultured cells with an expression vector containing the isolated FBN1/ribozyme core sequence of pU1/FIB but no U1 snRNA secondary structure, under the transcriptional control of the SV40 promoter, resulted in no discernible inhibitory effect on the expression of fibrillin-1 transcript or protein. The oligonucleotides described above containing the 24 highly conserved nucleotides of hammerhead ribozymes flanked by complementary sequence for 10 codons in the translation start site region of the FBN1 mRNA, were cloned into the SpeI and EcoRI restriction sites for the polylinker of pZeoSV (Invitrogen). Fetal fibroblasts were stably transfected with this vector. Immunohistochemical analysis of these clones was performed by methods identical to those described herein). These results suggest that selected properties of U1 snRNA and/or its promoter are contributing to the extreme efficiency of inhibition seen with the use of the chimeric cRNA.

Although the invention has been described with reference to the presently preferred embodiment, it should be understood that various modifications can be made without departing from the spirit of the invention. Accordingly, the invention is limited only by the following claims.

What is claimed is:

1. A nucleic acid construct for suppressing expression of a target gene, comprising:

an antisense nucleic acid sequence directed to said target gene;

an unmodified, naturally occurring 5' U1 snRNA stem loop structure 5' of said antisense nucleic acid sequence;

a pol II promoter region 5' of said 5' U1 snRNA stem loop structure; and a naturally occurring 3' U1 snRNA stem loop structure 3' of said antisense nucleic acid sequence, wherein said expression of said target gene is suppressed by at least 75% of the normal level of expression.

2. The nucleic acid construct of claim 1, wherein the promoter is a U1 snRNA promoter.

3. The nucleic acid construct of claim 1, wherein the promoter is a constitutive promoter.

4. The nucleic acid construct of claim 1, wherein the promoter is an inducible promoter.

5. The nucleic acid construct of claim 1, wherein the antisense nucleic acid is targeted to a region of a gene selected from the group consisting of rent-1, HPV E6, HIV, hyaluronic acid synthase, and fibrillin.

6. The nucleic acid construct of claim 1, further comprising a 5' trimethylguanosine cap.

7. The nucleic acid construct of claim 1, further comprising a ribozyme nucleic acid which specifically cleaves mRNA transcribed from said target gene wherein said ribozyme is located between the 5' and 3' stem loop structures.

8. The nucleic acid construct of claim 7, wherein the ribozyme nucleic acid is a hammerhead-type ribozyme.

9. The nucleic acid construct of claim 7, wherein a consensus sequence for ribozyme cleavage in a target nucleic acid is 5'-GUC-3' or 5'-GUA-3'.

10. A method for suppression of expression of a target gene comprising administering the nucleic acid construct of claim 1 to an isolated cell, wherein said construct is expressed at a level sufficient to suppress expression of said target gene.

11. The method of claim 10, further comprising:

administering a second nucleic acid encoding a wild-type polypeptide corresponding to the gene product of the target gene being suppressed, wherein the second nucleic acid is resistant to ribozyme cleavage and/or antisense inhibition.

* * * * *

UNITED STATES PATENT AND TRADEMARK OFFICE
CERTIFICATE OF CORRECTION

PATENT NO : 5,814,500
DATED : September 29, 1998
INVENTOR(S): Harry C. Dietz

It is certified that error appears in the above-identified patent and that said Letters Patent is hereby corrected as shown below:

At column 1, line 3, immediately following the title, please insert the following paragraph:

--STATEMENT REGARDING FEDERALLY SPONSORED RESEARCH

This work was supported by grants AR41135 and HL41135 awarded by the National Institutes of Health. The United States government may have certain rights to the invention.--

Signed and Sealed this

Twenty-seventh Day of March, 2001

*Attest:*

NICHOLAS P. GODICI

*Attesting Officer*   *Acting Director of the United States Patent and Trademark Office*